United States Patent [19]

Hansen

[11] Patent Number: 4,673,352
[45] Date of Patent: Jun. 16, 1987

[54] DEVICE FOR MEASURING RELATIVE JAW POSITIONS AND MOVEMENTS

[76] Inventor: Markus Hansen, Prinz-Albert-Strasse 63, D-5300 Bonn 1, Fed. Rep. of Germany

[21] Appl. No.: 815,713

[22] Filed: Jan. 2, 1986

[30] Foreign Application Priority Data

Jan. 10, 1985 [DE] Fed. Rep. of Germany ....... 3500605

[51] Int. Cl.⁴ .............................................. A61C 19/04
[52] U.S. Cl. ........................................ 433/69; 433/73; 128/777
[58] Field of Search ...................... 433/68, 69, 72, 73; 128/653, 777

[56] References Cited

U.S. PATENT DOCUMENTS

| | | | |
|---|---|---|---|
| 4,182,312 | 1/1980 | Mushabac | 433/68 |
| 4,303,077 | 12/1981 | Lewin et al. | 433/69 |
| 4,303,919 | 12/1981 | Dimeff | 433/68 |
| 4,330,276 | 5/1982 | Becker et al. | 433/69 |
| 4,354,836 | 10/1982 | Santoni | 433/73 |
| 4,447,207 | 5/1984 | Kataoka et al. | 433/69 |

FOREIGN PATENT DOCUMENTS 0043149 1/1982 European Pat. Off. ............ 128/777

Primary Examiner—John J. Wilson
Assistant Examiner—Adriene J. Lepiane
Attorney, Agent, or Firm—Spensley Horn Jubas & Lubitz

[57] ABSTRACT

The apparatus comprises a first holder (10) fixed stationarily relative to the upper jaw to the patient's head, and a second holder (16) which is secured to the lower jaw. The second holder contains a number of distributed transmitters (S1, S2, S3) which successively supply stepwise ultrasonic pulses. A supplied ultrasonic pulse is successively received by all of the receivers (E1, E2, E3) of the other holder (10). By the transit times, the distances between the receivers and the activated transmitter may be noted. Changes of the sound velocity are detected by a reference path (S4R, E3; S3, E4R) and used for the correction of the transit time signals. By means of an additional, freely movable holder which also carries a number of transmitters and which contains a scanning tip, the position, data of individual teeth or of other points of the mouth may be imputted into the computer.

6 Claims, 4 Drawing Figures

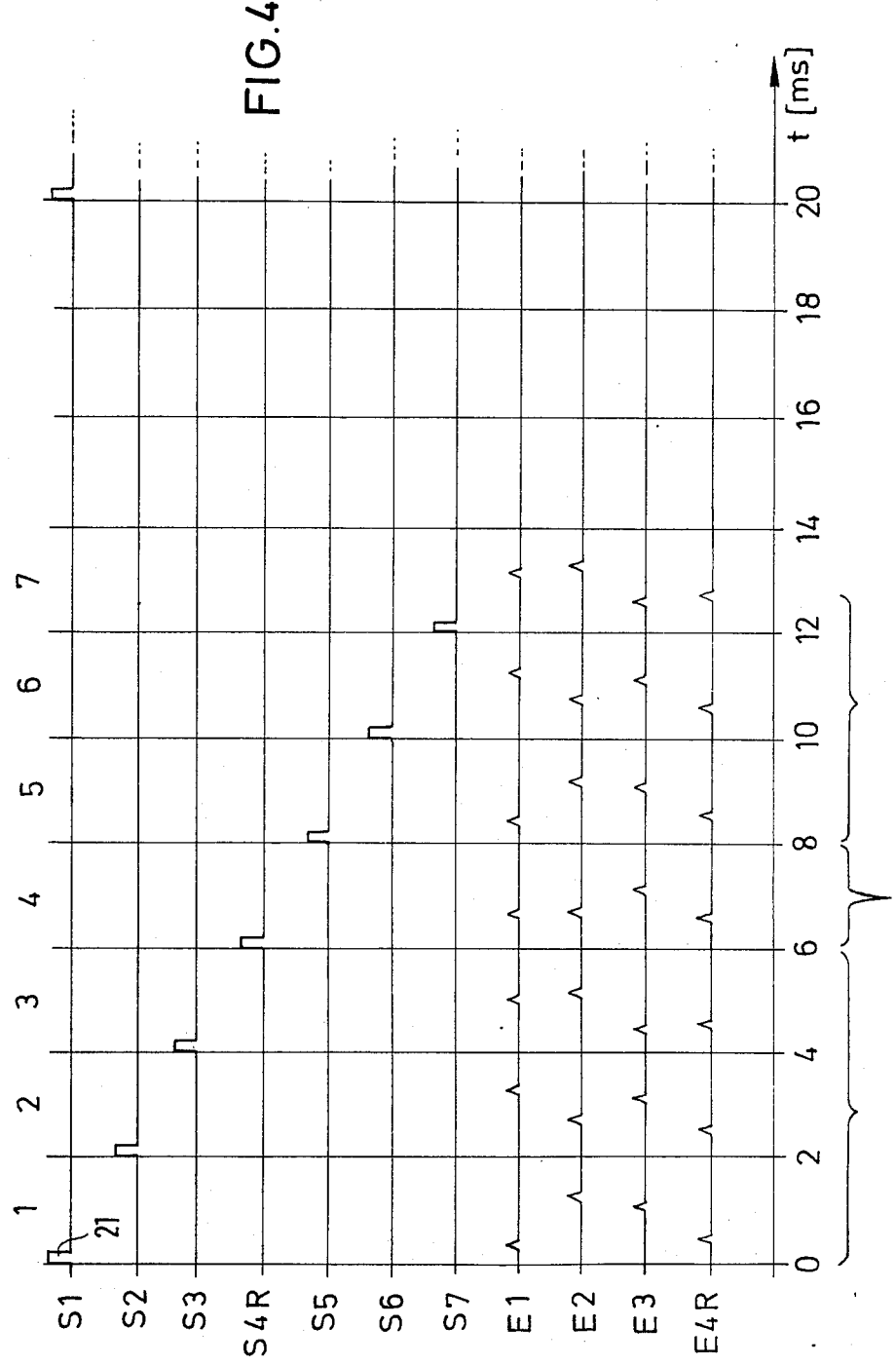

DEVICE FOR MEASURING RELATIVE JAW POSITIONS AND MOVEMENTS

BACKGROUND OF THE INVENTION

The invention relates to an apparatus for measuring the positions and movements of the lower jaw relative to the upper jaw comprising a first holder to be secured in a fixed relationship to the upper jaw to the patient's head, a second holder to be secured to the lower jaw and a plurality of distance measuring means including a respective transmitter and receiver which are provided at the holders to determine the positions of the holders relative to each other.

In a known device of this type (EP laid open publication No. 0 025 201), the holders are jaw plates which are provided in the patient's mouth. The jaw plate of the upper jaw includes one sole transmitter, while a plurality of receivers are distributed at the jaw plate of the lower jaw, each receiver forming with the transmitter a distance measuring means. If the patient moves his lower jaw, the changing distances between each receiver and the transmitter are recorded. In an articulator containing the models of the lower and upper jaws, the jaw movements may be reproduced under control by the recorded data. With the use of three distance measurements, it is not possible, by means of the known system, to clearly identify all jaw movements. While due to the design of the measuring system, the jaw movements may be reproduced in an articulator, no exact measuring of the jaw and mouth movements is possible for all that. Above all, it is impossible to determine and check at the patient's head the articulation axis between lower and upper jaw whose position constantly changes during masticating movements.

It is the object of the invention to provide an apparatus of the foregoing type which allows to exactly cover and analyse the movements of the lower jaw relative to the upper jaw by clearly considering all of the degrees of freedom of the system.

SUMMARY OF THE INVENTION

The problem is solved according to the invention in that at least three successively activatable transmitters of ultrasonic signals are mounted at the one holder, that at the other holder, at least three receivers of ultrasonic signals are fixed of which each receiver is responsive to the ultrasonic signals supplied by all the transmitters of the one holder, and that the intervals at which the transmitters are activated successively are longer than the maximum transit time of the ultrasonic signals between one transmitter and one receiver.

The transmitters and the receivers of the apparatus of the invention form a multiplex system in which the activation signals of the transmitters define a corresponding time channel. At the beginning of its channel time, each transmitter supplies a short pulse. During the channel time, the individual receivers receive the ultrasonic pulse, the receiving time depending upon the distance between the activated transmitter and the corresponding receiver. Within the channel time, all of the receivers are responsive to the signal supplied by the activated transmitter. Thus, within one channel time, the number of distance values obtained corresponds to the number of the receivers. In the subsequent channel time, another transmitter is activated, and again, the number of obtained distance values is in accordance with the number of the receivers. Preferably, three transmitters are provided at one holder and three receivers are provided at the other holder. In case of three transmitters and three receivers, one may obtain nine distance data. In view of the six degrees of freedom allowed for the movement of the lower jaw relative to the upper jaw (three translatory and three rotary degrees of freedom), six distance measurements would be sufficient to cover clearly all movements. Nine measured values are redundant and contribute to a safer result.

A computer for processing the distance data determines the position of the lower holder relative to the assumed stationary position of the upper holder. The calculations are performed with the use of a coordinate system which is stationary relative to the upper holder and in which the position and alignment of the lower holder are calculated accordingly. However, the dentist is not yet able this way to determine the movements performed by a specific point of the lower jaw, e.g. by a tooth, in relation to a specific point of the upper jaw. To permit a mutual coordination of teeth, bone parts and other elements of the mouth, a preferred further embodiment of the invention provides a freely movable third holder containing a scanning stylus and carrying a transmitter or receiver to form with the receivers or transmitters of the first holder additional distance measuring systems. From the values of the additional distance measuring systems, a computer calculates the position data of the scanning stylus with respect to one coordinate point which is stationary relative to the first holder.

By means of the third holder which contains the scanning stylus, the dentist may feed the computer with specific points of the lower jaw or of other parts of the mouth in order to subsequently obtain a draft or a reproduction on the screen etc. e.g. of the trajectory of said points in case of different movements of the mouth. The third holder which cooperates with the stationary first holder allows the dentist to input into the computer position data of interesting points of the lower jaw and/or of the upper jaw e.g. a point of the masticatory surface of an artificial tooth to be implanted. If upper and lower jaws are pressed against one another, one may find out as to whether the masticatory surface of the artificial tooth takes the right position and whether the closing movement of the mouth is not affected. If necessary, the position of the masticatory surface may be corrected.

Further, the third holder having the scanning stylus may be used to determine the articular axis about which, during mastication, the lower jaw is turned relative to the upper jaw. Said joint axis is not stationary, but its position changes responsive to the opening position of the mouth. If the patient makes masticating movements, while the holders are fixed to his jaws, the position of the articular axis may be calculated by the computer. The dentist may set the third holder so that the scanning tip points near the cheekbone to a site which is supposed to be on the axis of articulation within a specific opening range of the mouth.

Subsequently, the computer will check whether the scanning stylus is on its calculated axis of rotation, and corrected values may be supplied to the dentist, if necessary. By means of the computer, the dentist may determine the exact position of the articular axis at his patient's head. This is important for the later setting of the articular axis of the articulator containing plaster models of the upper and lower jaws to ensure that the movement of the plaster model of the lower jaw is identical to the movement of the lower jaw in the mouth of the patient.

Preferably, the configuration and the mutually spaced relationship of the transmitters or receivers of the third holder is similar to the arrangement of transmitters or receivers of the second holder. This will facilitate the programming of the computer, because distance signals referring to the third holder may be calculated in the same way as those referring to the second holder which is fixed to the lower jaw of the patient.

The use of ultrasonic signals for measuring distances is problematic in that the sound velocity is influenced by temperature and humidity of the air. The measured paths being exposed to the warm and humid breath of the patient, measuring errors may occur, which, according to a further embodiment of the invention, are eliminated in that at the first holder and/or at the second holder, there is provided at least one reference measuring unit including a transmitter and a receiver of a constant spaced relationship and that the transit time of the ultrasonic signals between the transmitter and receiver of the reference measuring unit supply a correction value for the signals of the remaining distance measuring means.

The reference measuring unit is formed of a transmitter and of a receiver spaced mutually at a defined distance. The transit time of the ultrasonic signals between said transmitter and said receiver is used as a reference value to correct the signals of the other distance measuring units. By this means, changes of the sound velocity near the measuring system may be compensated.

One embodiment of the invention will be explained hereunder in more detail with reference to the drawings.

BRIEF DESCRIPTION OF THE DRAWINGS

FIG. 4 is a pulse diagram of the transmitted and received signals.

DETAILED DESCRIPTION OF THE DRAWINGS

Figure 1:
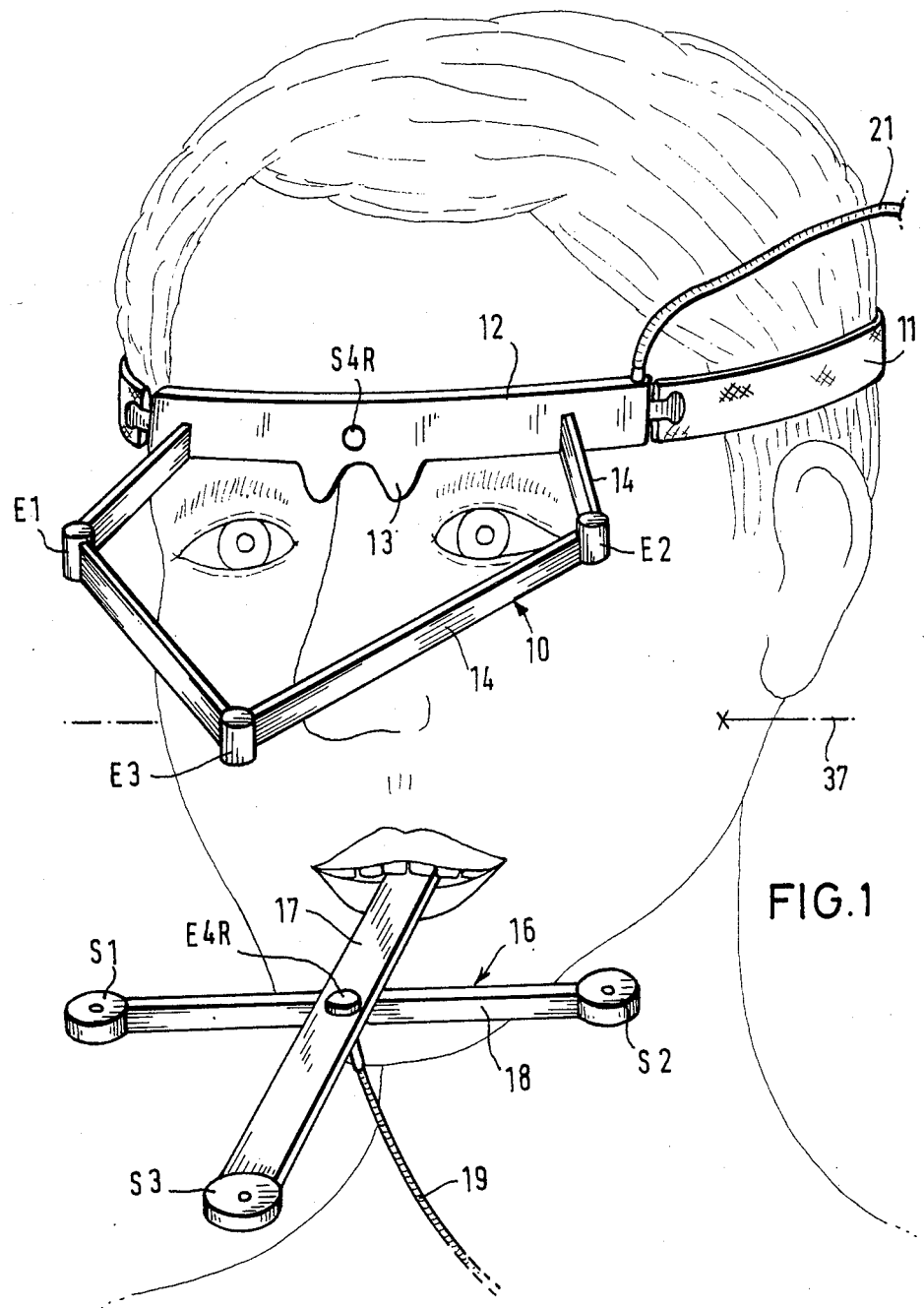
FIG. 1 is a perspective view of the measuring system applied to the patient.

As evident from FIG. 1, the patient's head is provided with the first holder 10 including a headband 11 placed around the head, the holder 10 consisting of a rigid frame having a bent portion 12 which is flatly adapted to the patient's front and supported on the root of his nose by a carrier 13. From the bent portion 12, there project frontally struts 14 to which three receivers E1,E2 and E3 are secured of which the two lateral receivers E1 and E2 are equally spaced from the bent portion 12, while the distance between the central receiver E3 and the element 12 is larger. The plan view of the receivers E1,E2 and E3 shows that they are placed at the corners of a horizontal equal-sided triangle. The upper jaw (maxilla) being immobile relative to the head, the first holder 10 fitted at the head taking a fixed position relative to the maxilla.

The second holder 16 is fixed by a (non-illustrated) brace to the patient's lower jaw (mandible) and comprises two struts 17,18 intersecting at right angles and of which strut 17 extends between the patient's lips through his mouth. The free ends of the struts 17 and 18 are provided with three transisters S1, S2, S3 which, preferably, are disposed at the corner points of a triangle which is congruent to that formed by the receivers E1,E2, and E3.

Figure 3:
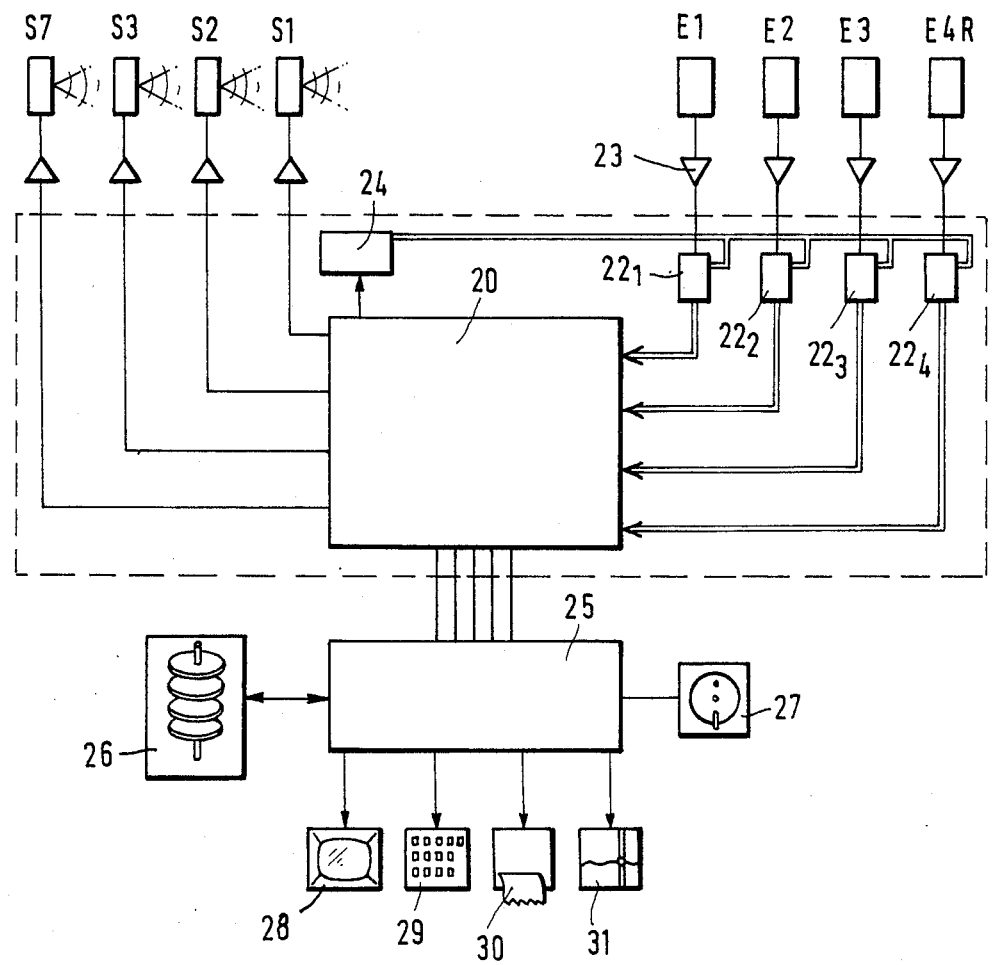
FIG. 3 is a wiring diagram of the apparatus.

Transmitters S1, S2, S3 are connected by cables 19 to the measuring computer 20 (FIG. 3), while the receivers E1,E2 and E3 are connected by cables 21 to the main computer. Transmitters S1,S2 and S3 are activated successively to produce a short ultrasonic pulse 21 which consists of a pressure wave whose rise slope should be inferior to 10 $\mu$s. If transmitter S1 transmits the ultrasonic pulse 21, the latter is received at different times by the receivers E1,E2 and E3, the time intervals being dictated by the distance between the respective receiver and the transmitter S1.

Upon activation of one of the transmitters, the measuring computer 20 supplies to a counter 24 a pulse clock of 8 MHz to count up from zero the count of said counter. The count of counter 24 is transmitted to the inputs of the holding circuits $22_1, 22_2, 22_3$ which are assigned to the individual receivers $E_1, E_2$ and $E_3$. If the ultrasonic pulse is received by one of the receivers, a pulse is supplied by it through an amplifier 23 to the associated holding circuit which then will retain the count of counter 24. By this means, at the end of a measuring interval, each holding circuit contains a count which is proportional to the transit time of the ultrasonic signals between the transmitter and the respective receiver. Subsequently, the contents of the holding circuits are inputted into the measuring computer 20.

The measuring computer 20 is connected to the main computer 25 which receives the distance data to calculate by arithmetic processing the position of the lower jaw on the basis of a coordinate system which is stationary relative to the upper jaw. A number of peripheral instruments is connected to the main computer 25, such as for inst. a disk storage unit 26, a floppy disk unit 27, a display device 28, an input keyboard 29, a printer 30 and a plotter 31.

In case of the disclosed embodiment, an interval of 2 ms is available in which all receivers receive the ultrasonic pulse supplied by one transmitter. The transit time of the ultrasonic pulses being inferior to 20 ms, sufficient time is available at the end of each interval to feed the distance data from the holding circuits 22 into the measuring computer 20 and to carry out various calculations.

The second holder 16 including the transmitters S1, S2 and S3 is provided additionally with a receiver E4R which is positioned at the point of intersection of struts 17 and 18. Together with one transmitter of said holder 16, the receiver E4R forms a reference measuring path. It receives also the signals of all of the three transmitters S1, S2 and S3, although only the signal of one of the transmitters is to be evaluated. The control of the holding circuit $22_4$ of said receiver E4R is made in the same way as in case of the holding circuits of the remaining receivers, and the value supplied to the main computer 20 corresponds to the established distance of the receiver E4R from one of the transmitters S1, S2 or S3. By comparison or proportional consideration of this value with regard to a value corresponding to the normal transit time between a transmitter and a receiver, a correction value is determined to correct the other distance values. By this means, the sound velocity in the vicinity of the patient's mouth is determined subject to the prevailing momentary conditions to be considered for the measurement.

Alternatively or additionally, the first holder 10 carrying the receivers E1, E2 and E3 is adapted to include a transmitter S4R fixed thereto and to which, according to the pulse diagram of FIG. 4, an interval of its own of 2 ms is assigned. The transit time of the ultrasonic signal from the transmitter S4R to one of the receivers E1,E2 or E3 is determined in order to obtain a correction signal for the remaining transit time signals.

While, with the device disclosed hitherto, position changes of the lower jaw relative to the upper jaw may be detected, it is not possible to determine therewih for inst. the positions of the teeth of the lower jaw relative to the teeth positions of the upper jaw. As evident from FIG. 2, there is provided a third holder 33 which consists of two intersecting struts 34, 35, of which the two ends of strut 35 include two transmitters S5 and S6, while the one end of strut 34 is equipped with a third transmitter S7, and the other, end of strut 34 is designed to form a scanning tip 36. The third holder is not secured to the patient's body, but it may be freely handled by the dentist to apply the scanning tip 36 to any optional points, e.g. to a tooth. To each transmitter S5, S6, and S7, an interval of 2 ms(milliseconds) is assigned during which the distances from the respective transmitter to each of the receivers E1, E2 and E3 of the fixed holder 10 is determined. From the new distance values, the computer calculates the position of the scanning tip 36 relative to the coordinate system which, with respect to the first holder 10 is fixed. For inst. by means of the scanning tip 36, the dentist may indicate to a point in the patient's mouth to input the position data of the point into the computer. Thereafter, the dentist uses the scanning tip 39 to direct it to another point in the patient's mouth and to also input the position data of the second point into the computer. If the movements of the lower jaw are subsequently recorded, the relative movements of the two measured points may be shown in a curve.

Further, the second holder 33 may be used to control the masticatory axis 37 about which, during mastication, the lower jaw is moved relative to the upper jaw. The position of the masticatory axis 37 (FIG. 1) is not stationary, but it is displaced responsive to the opening position of the mouth.

The scanning tip 36 may be directed by the dentist to a point near the cheekbone which point is supposed to be situated on the masticatory axis 37. Since the positioned of the masticatory axis 37 has been defined by the computer, the latter may check as to whether the scanning tip is positioned on the masticatory axis or at which distance it is spaced therefrom. By this means, by moving the scanning tip outside the patient's mouth, the dentist may determine the position of the masticatory axis 37 in case of a specific opening position of the mouth, and corresponding instructions may be given to the dental technician in view of the adjustment of the articulator. To determine the masticatory axis, use may be made, instead of holder 33, of a modified holder wherein one end of the strut 34 is shaped angularly.

The pulse diagram illustrated in FIG. 4 shows that the first three measuring intervals of 2 ms each are assigned to the transmitters S1, S2 and S3 in order to determine the position of the second holder 16 relative to the first holder 10. In the fourth interval, the reference measuring is made, i.e. the distance value is determined between the transmitter S4R and one of the receivers of the same holder 10, e.g. receiver E3. During the fifth to seventh intervals, there is measured the position of the third holder 33 or of the scanning tip 36 by successively activating the transmitters S5, S6 and S7. Such a measuring cycle requires 14 ms. An interval of 6 ms may follow thereafter, and the measuring cycle will be repeated again. By this means, the system is adapted to also follow quick movements of the lower jaw because each measuring value is taken 50 times per second.

Figure 2:
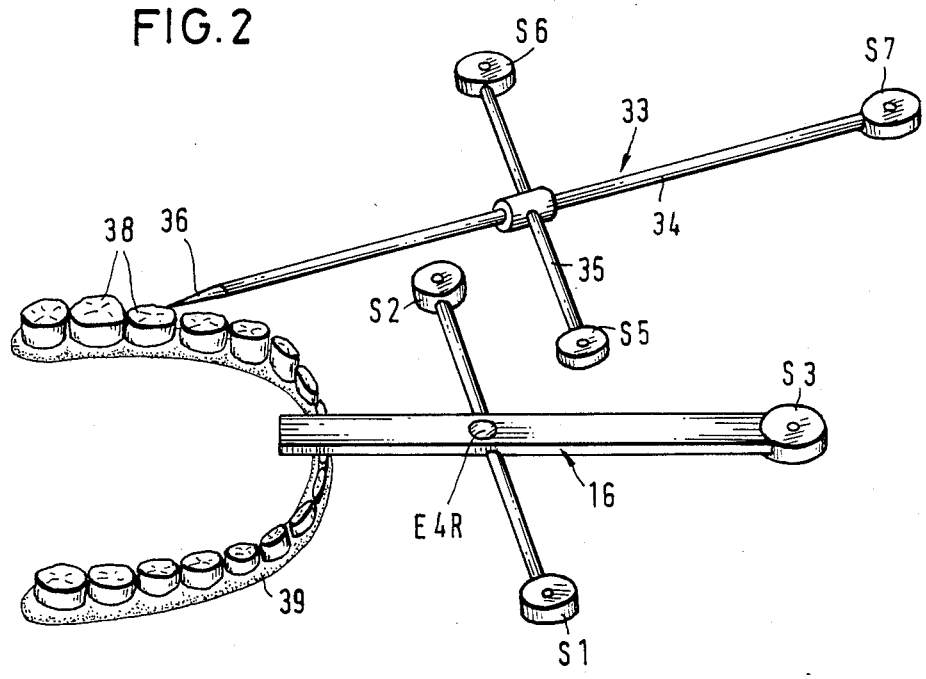
FIG. 2 is a view of the second holder and of the third holder.

FIG. 2 shows a tooth brace 39 to which the second holder 16 is secured, said tooth brace 39 being fixed to the patient's lower jaw. Reference numeral 38 designates the teeth of the lower jaw.

What is claimed is:

1. Apparatus for measuring the positions and movements of the lower jaw relative to the upper jaw, comprising a rigid first holder to be secured in a fixed relationship to the upper jaw to the patient's head, a rigid second holder to be secured to the lower jaw and a plurality of distance measuring devices including a respective transmitter and receiver which are provided at the holders to determine the positions of the holders relative to each other, wherein at one of said first and second holders, there are fixed at least three successively activatable transmitters for ultrasonic signals, at the other holder there are mounted at least three receivers for ultrasonic signals, means for activating the transmitters in succession with intervals therebetween that are longer than the maximum transit time of the ultrasonic signals between a transmitter and a receiver, and each of said at least three receivers having means for receiving the ultrasonic signals of all the transmitters of the one holder, whereby a distance value between a transmitter and each of the receivers can be determined for each of the transmitters.

2. Apparatus according to claim 1, wherein a freely movable third holder comprising a scanning tip and carrying either a transmitter or receiver and forming with the receivers or transmitters, respectively, of the first holder additional distance measuring untis, a computer calculating from the values of the additional distance measuring means position data of the scanning tip relative to one point of coordinates being stationary relative to the first holder.

3. Apparatus according to claim 2, wherein the configuration and mutual relationship of the transmitters of the third holder are substantially the same as those of the transmitters or receivers of the second holder.

4. Apparatus according to claim 1, wherein at least one of the first holder and second holder is provided with at least one reference measuring unit including a transmitter and a receiver, mutually spaced at a constant distance, such that the transit time of the ultrasonic signals between transmitter and receiver of the reference unit supplies a correction value for the signals of the remaining distance measuring means.

5. The apparatus of claim 1 further including a freely movable third holder having a scanning tip provided with either a transmitter or receiver, thereby forming an additional distance measuring unit with the distance measuring devices of the first holder; and
a computer using the position data of the scanning tip distance measuring device to calculate position data of the scanning tip relative to the first holder.

6. An apparatus for measuring the positions and movements of a patient's lower jaw relative to the patient's upper jaw comprising:

- rigid first and second holders, one holder being secured to the patient's head in a fixed relationship to the upper jaw and the other holder being secured to the lower jaw; and
- a plurality of ultrasonic transmitter/receiver pairs provided at positions on the first and second holders, wherein at least three transmitters are fixed on the first holder and at least three receivers are mounted at the other holder, means for activating the transmitters in succession with intervals therebetween that are longer than the maximum transit time of the ultrasonic signals between a transmitter and a receiver, and each of said at least three receivers having means for receiving the ultrasonic signals of all the transmitters of the one holder, whereby a distance value between a transmitter and each of the receivers can be determined for each of the transmitters.

* * * * *